United States Patent
Agus

(10) Patent No.: US 7,803,546 B2
(45) Date of Patent: Sep. 28, 2010

(54) METHOD OF SCREENING FOR SENSITIVITY TO KINASE INHIBITOR THERAPY

(75) Inventor: David B. Agus, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 547 days.

(21) Appl. No.: 11/678,420

(22) Filed: Feb. 23, 2007

(65) Prior Publication Data

US 2007/0141621 A1 Jun. 21, 2007

Related U.S. Application Data

(62) Division of application No. 11/359,826, filed on Feb. 22, 2006, now abandoned, which is a division of application No. 10/454,323, filed on Jun. 4, 2003, now Pat. No. 7,384,940.

(60) Provisional application No. 60/386,622, filed on Jun. 5, 2002.

(51) Int. Cl.
C12Q 1/68 (2006.01)
G01N 33/574 (2006.01)
C07H 21/00 (2006.01)

(52) U.S. Cl. .................... 435/6; 435/7.21; 435/7.23; 536/23.1

(58) Field of Classification Search .............. None
See application file for complete search history.

(56) References Cited

U.S. PATENT DOCUMENTS

| 2002/0039764 A1* | 4/2002 | Rosen et al. ............... 435/69.1 |
| 2002/0110563 A1* | 8/2002 | Reed et al. ............... 424/155.1 |
| 2003/0144252 A1 | 7/2003 | Furr |
| 2004/0029151 A1* | 2/2004 | Mahadevappa et al. ........ 435/6 |
| 2005/0059012 A1* | 3/2005 | Afar et al. ...................... 435/6 |
| 2005/0244419 A1 | 11/2005 | Tosi et al. ................... 424/184 |
| 2008/0138838 A1* | 6/2008 | Afar et al. ................... 435/7.23 |

FOREIGN PATENT DOCUMENTS

| WO | 01/32155 | 5/2001 |
| WO | WO 01/32155 A2 | 5/2001 |
| WO | 03/103676 | 12/2003 |
| WO | WO 03/103676 A2 * | 12/2003 |

OTHER PUBLICATIONS

Chen et al. (Genomics 1997, 41:40-48).*
U. Alon et al., "Broad Patterns of Gene Expression Revealed by Clustering Analysis of Tumor and Normal Colon Tissues Probed by Oligonucleotide Arrays," *Proc. Natl. Acad. Sci. USA*, vol. 96, pp. 6745-6750 (1999).
E. Göker et al., "Amplificaton of the Dihydrofolate Reductase Gene is a Mechanism of Acquired Resistance to Methotrexate in Patients with Acute Lymphoblastic Leukemia and is Correlated with p53 Gene Mutations," *Blood*, vol. 86(2), pp. 677-684 (1995).
S. Roumiantsev et al., "Clinical Resistance to the Kinase Inhibitor STI-571 in Chronic Myeloid Leukemia by Mutation of Tyr-253 in the Abl Kinase Domain P-loop," *Proc. Natl. Acad. Sci. USA*, vol. 99(16), pp. 10700-10705 (2002).
N. Shah et al., "Multiple *BCR-ABL* Kinase Domain Mutations Confer Polyclonal Resistance to the Tyrosine Kinase Inhibitor Imatinib (STI571) in Chronic Phase and Blast Crisis Chronic Myeloid Leukemia," *Cancer Cell*, vol. 2, pp. 117-125 (2002).
Various Authors, "Roots of Clinical Resistance to STI-571 Cancer Therapy," *Science:Technical Comments*, vol. 293, p. 2163a (2001).
Kelly, Helen C., et al., "An Oral Epidermal Growth Factor Receptor Tyrosine Kinase Inhibitor (EGFR-TKI): Pharmacokinetics in a Phase I Study of Patients with Advanced Cancer", *AstraZeneca Pharmaceuticals*, Macclesfield, United Kingdom, 2000.
Sirotnak, Francis M., et al., "Efficacy of Cytotoxic Agents Against Human Tumor Xenografts Is Markedly Enhanced by Coadministration of ZD1839 (Iressa), an Inhibitor of EBFR Tyrosine Kinsase," *Clinical Cancer Research*, vol. 6, 4885-4892, Dec. 2000.
Sirotnak, Francis M., et al., "Studies with CWR22 Xenografts in Nude Mice Suggest That ZD1839 May Have a Role in the Treatment of Both Androgen-dependent and Androgen-independent Human Prostate Cancer," *Clinical Cancer Research*, vol. 8, 3870-3876, Dec. 2002.
LoRusso, Patricia M., "Phase I Studies of ZD1839 in Patients with Common Solid Tumors," *Seminars in Oncology*, vol. 30, No. 1, Suppl. 1 (Feb. 2003); pp. 21-29.
U.S. Appl. No. 11/234,586, filed Sep. 2005, Agus, et al.
Ciardiello F and Tortora G, "Anti-epidermal growth factor receptor drugs in cancer therapy," Expert Opinion Investig. Drugs 2002 vol. 11(6): 755-768.
Molina MA, et al. ("Trastuzumab (Herceptin), a humanized anti-HER2 receptor monoclonal antibody . . . ," 2001 Cancer Research 61: 4744-4749.

(Continued)

*Primary Examiner*—Peter J Reddig
(74) *Attorney, Agent, or Firm*—Seth D. Levy; Davis Wright Tremaine LLP

(57) ABSTRACT

Described herein are methods for treating cancer and other disease conditions in individuals who have either developed a resistance to conventional tyrosine kinase inhibitor (TKI) therapy or who are non-responsive ab initio to conventional TKI therapy. In various embodiments, the methods include administering to a patient a resistance-surmounting quantity of a TKI on a weekly or semi-weekly basis. Alternate embodiments of the present invention include a diagnostic method for assessing an individual's probability of being resistant to TKI therapy, based upon an expression level of epithelial membrane protein-1 (EMP-1); one of the genes believed to be responsible for TKI resistance. The methods of the present invention may be particularly useful in the treatment of lung, breast, prostate, ovarian, brain and colon cancers. The methods of the present invention may be effective in blocking the HER-2 kinase domain either in addition to or in lieu of blocking the EGFR kinase domain.

4 Claims, 14 Drawing Sheets

OTHER PUBLICATIONS

Cecil, Textbook of Medicine, 21st Edition (2000), Goldman & Bennett (Editors), W.B. Saunders Company (Publisher), Chapter 198, pp. 1060-1074.

"Technical Comments: Roots of clinical resistant to STI-571 cancer therapy," Sep. 2001 Science 293: 2163a, provided by Applicant on PTO 1449.

Ciardiello and Tortora ("A novel approach in the treatment of cancer: targeting the epidermal growth factor receptor," Oct. 2001 Clinical Cancer Research 7: 2958-2970.

Larsen SS, et al. ("Acquired antiestrogen resistance in MCF-7 human breast cancer sublines is not accomplished by altered expression of receptors in the Erb-B family," 1999 Breast Cancer Research and Treatment 58: 41-56).

Arora, A. et al., Role of Tyrosine Kinase Inhibitors in Cancer Therapy, J Pharmacol Exp Ther, (2005) 315(3):971-9.

Baselga, J. et al., Phase I Safety, Pharmacokinetic, and Pharmacodynamic Trial of ZD1839, a Selective Oral Epiderman Growth Factor Receptor Tyrosine Kinase Inhibitor, in Patients With Five Selected Solid Tumor Types, Journal of Clinical Oncology, (2002) 20(21):4292-4302.

Carter, T.A. et al., Inhibition of Drug-Resistant Mutants of ABL, KIT, and EGF Receptor Kinases, PNAS, (2005)102(31)11011-11016.

Iressa product description, AstraZeneca, (2003).

Ranson, M., ZD1839 (Iressa™): For More Than Just Non-Small Cell Lung Cancer, The Oncologist, (2002) 9(suppl 4)16-24.

Tuma, R.S., New Studies Look Beyond EGFR Mutations for Clues to Sensitivity to Erlotinib, Journal of the National Cancer Institute (2005) 97(14):1028-29.

Greenbaum et al. (Genome Biology, 2003, vol. 4, Issue 9, pp. 117.1-117.8).

Brennan et al. (J. Autoimmunity, 1989, 2 (suppl.): 177-186).

Zimmer (Cell Motility and the Cytoskeleton, 1991. 20:325-337).

Heil et al. (Laboratory Investigation, 1995, 73: 492-496).

Fu et al. (EMBO J., 1996, 15:4392-4401).

Vallejo et al. (Biochimie, 2000 82:1129-1133).

Jang et al. (Clinical Exp. Metastasis, 1997, 15: 469-483).

Tockman et al (Cancer Res., 1992, 52:2711s-2718s).

Busken, C et al, (Digestive Disease Week Abstracts and Itinerary Planner, 2003, abstract No. 850).

Krontiris and Capizzi (Internal Medicine, 4th Edition, Editor-in-chief Jay Stein, Elsevier Science, 1994 Chapters 71-72, pp. 699-729).

Carter, S. K. et al. (Chemotherapy of Cancer; Second edition; John Wiley & Sons : New York, 1981; appendix C).

Stites et al (Medical Immunology, 9th Ed, Appleton and Lange, Stamford, 1997, p. 250-251).

Taber's Cyclopedic Medical Dictionary (1985, F.A. Davis Company, Philadelphia, p. 274).

Kelly, H.C. et al., ZD1839 ('Iressa') an oral epidermal growth factor receptor tyrosine kinase inhibitor (EGFR-TKI): Pharmacokinetics in a phase 1 study of patients with advanced cancer, Proceedings of the Annual Meeting of the American Association for Cancer Research, New York, NY, (Mar. 2000), p. 612 (Abstract).

LoRusso, P.M., Phase I studies of ZD1839 in patients with common solid tumors, Seminars in Oncology, (Feb. 2003), vol. 30, No. 1, Suppl. 1, pp. 21-29.

Sirotnak, F.M. et al., Efficacy of cytotoxic agents against human tumor xenografts is markedly enhanced by coadministration of ZD1839 (Iressa), an inhibitor of EGFR tyrosine kinase, Clinical Cancer Research, (Dec. 2000), 6:4885-4892.

Sirotnak, F.M. et al., Studies with CWR22 xenografts in nude mice suggest that ZD1839 may have a role in the treatment of both androgen-dependent and androgen-independent human prostate cancer, Clinical Cancer Research, (Dec. 2002), 8:3870-3876.

Bridges, A.J., Current progress towards the development of tyrosine kinase inhibitors as anticancer agents, Emerging Drugs, Ashley Publications, London, GB, (1998), 3:279-292.

Jain, A. et al., Epithelial membrane protein-1 is a biomarker of gefitinib resistance, Proceedings of the National Academy of Sciences of the United States of America, (Aug. 16, 2005), 102:33, pp. 11858-11863.

Woodburn, J.R., The epidermal growth factor receptor and its inhibitors in cancer therapy, Pharmacology and therapeutics, Elsevier, GB, (1999), 82:2/3, pp. 241-250.

* cited by examiner

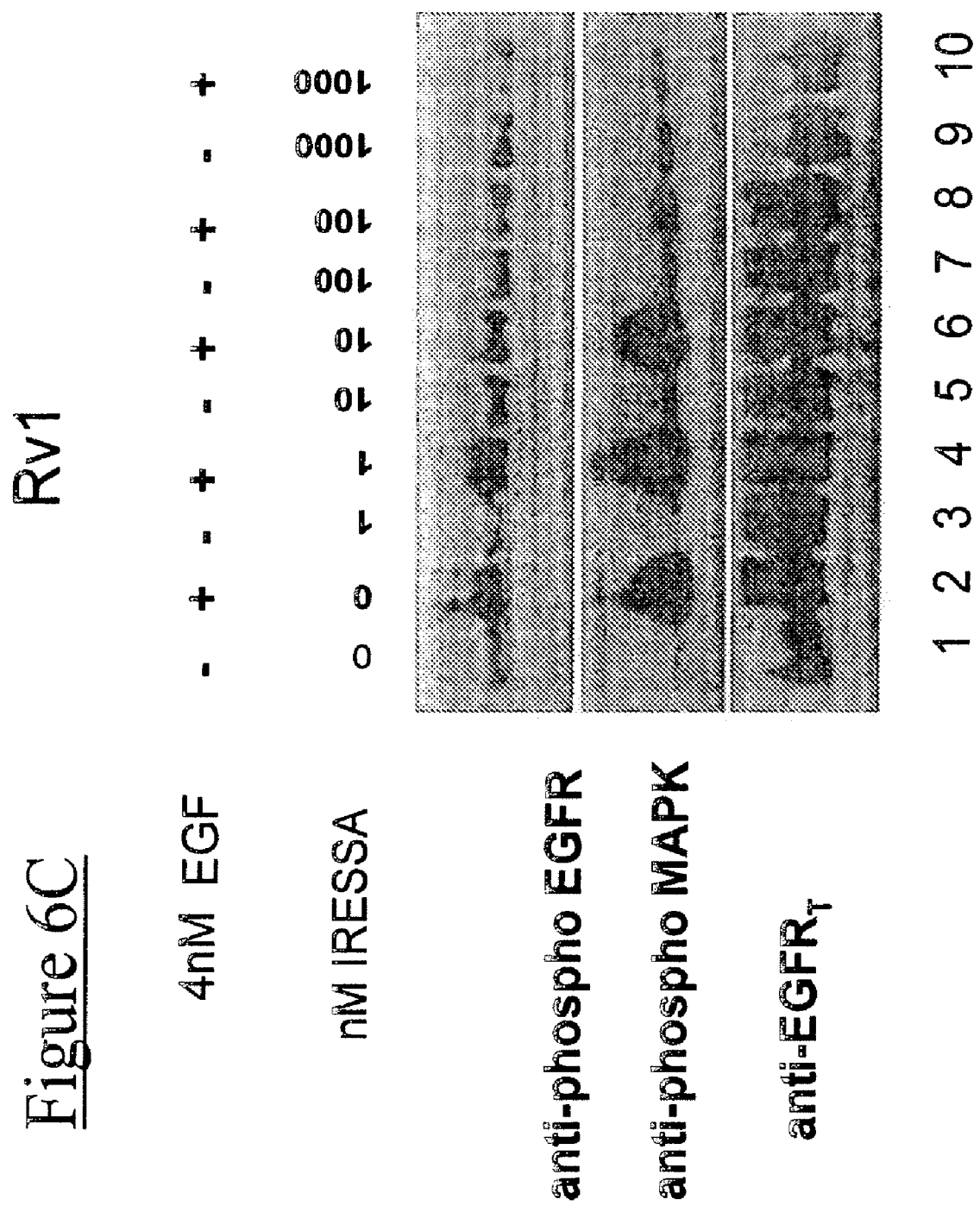

METHOD OF SCREENING FOR SENSITIVITY TO KINASE INHIBITOR THERAPY

RELATED APPLICATIONS

This application claims the benefit of priority under 35 U.S.C. §121 as a divisional of U.S. patent application Ser. No. 11/359,826 filed Feb. 22, 2006, now abandoned, which itself is a divisional of U.S. patent application Ser. No. 10/454,323, filed Jun. 4, 2003, now U.S. Pat. No. 7,384,940, which claims the benefit of priority under 35 U.S.C. §119 of U.S. provisional application Ser. No. 60/386,622, filed Jun. 5, 2002, the contents of which are hereby incorporated by reference.

FEDERAL SUPPORT

The U.S. Government has a paid-up license in this invention and the right in limited circumstances to require the patent owner to license others on reasonable terms as provided for by the terms of Grant No. 1P50CA092131 awarded by the National Institutes of Health.

PARTIES TO A JOINT RESEARCH AGREEMENT

At least some of the subject matter disclosed in this patent application was developed under and within the scope of a joint research agreement between Cedars-Sinai Medical Center and Eos Biotechnology, Inc.

FIELD OF THE INVENTION

Embodiments of the present invention are directed to methods for treating and preventing disease conditions, such as cancer, particularly in those individuals who have developed a resistance or who are not responsive ab initio to tyrosine kinase inhibitor (TKI) therapy.

BACKGROUND OF THE INVENTION

It is believed that cancer in humans is linked to the activity of non-viral, endogenous oncogenes, and that a substantial portion of these oncogenes code for protein tyrosine kinases. Ligand-mediated receptor tyrosine kinase inhibitors (RTKs), in particular, form a significant subgroup of these oncogenes, and are believed to function as "master switches" for a coordinated cellular communication network that regulates the normal proliferation of eukaryotic cells. Approximately sixty such RTKs have been identified to date; their respective cell signaling pathways having been studied in detail. Moreover, misregulation of RTK signaling pathways has been observed in various types of human cancer, suggesting that signal transduction therapy may be a useful therapeutic modality for the treatment of cancer. Other disease conditions in which RTKs play a pivotal role might also benefit from such therapy. One noteworthy success in this area is imatinib mesylate (available from Novartis Pharmaceuticals Corporation under the tradename GLEEVEC; hereinafter "GLEEVEC"); it is effective in the treatment of Philadelphia chromosome positive (Ph+) chronic myeloid leukemia (CML) by inhibiting translocation of the fusion gene responsible for BCR-ABL tyrosine kinase.

A promising set of targets for therapeutic intervention in the treatment of cancer includes the members of the HER-kinase axis. They are frequently upregulated in solid epithelial tumors of, by way of example, the prostate, lung and breast, and are also upregulated in glioblastoma tumors. Epidermal growth factor receptor (EGFR) is a member of the HER-kinase axis, and has been the target of choice for the development of several different cancer therapies. EGFR tyrosine kinase inhibitors (EGFR-TKIs) are among these therapies, since the reversible phosphorylation of tyrosine residues is required for activation of the EGFR pathway. In other words, EGFR-TKIs block a cell surface receptor responsible for triggering and/or maintaining the cell signaling pathway that induces tumor cell growth and division. Specifically, it is believed that these inhibitors interfere with the EGFR kinase domain, referred to as HER-1. Among the more promising EGFR-TKIs are three series of compounds: quinazolines, pyridopyrimidines and pyrrolopyrimidines.

Two of the more advanced compounds in clinical development include Gefitnib (compound ZD1839 developed by AstraZeneca UK Ltd.; available under the tradename IRESSA; hereinafter "IRESSA" and Erlotinib (compound OSI-774 developed by Genentech, Inc. and OSI Pharmaceuticals, Inc.; available under the tradename TARCEVA; hereinafter "TARCEVA"); both have generated encouraging clinical results. Conventional prostate cancer treatment with both IRESSA and TARCEVA involves the daily, oral administration of no more than 500 mg of the respective compounds. In May, 2003, IRESSA became the first of these products to reach the United States market, when it was approved for the treatment of advanced non-small cell lung cancer patients.

IRESSA is an orally active quinazoline that functions by directly inhibiting tyrosine kinase phosphorylation on the EGFR molecule. It competes for the adenosine triphosphate (ATP) binding site, leading to suppression of the HER-kinase axis. The exact mechanism of the IRESSA response is not completely understood, however, studies suggest that the presence of EGFR is a necessary prerequisite for its action.

A significant limitation in using these compounds is that recipients thereof may develop a resistance to their therapeutic effects after they initially respond to therapy, or they may not respond to EGFR-TKIs to any measurable degree ab initio. In fact, only 10-15 percent of advanced non-small cell lung cancer patients respond to EGFR kinase inhibitors. Thus, although the compounds may, at first, exhibit strong anti-tumor properties, they may soon become less potent or entirely ineffective in the treatment of cancer. Moreover, since medical research has heretofore not elucidated the biomolecular or pathological mechanism responsible for this resistance, patients who have exhibited such resistance to date have been left with few therapeutic alternatives to treat their disease. For patients that develop resistance, this potentially life-saving therapeutic mechanism did not achieve what they had hoped for and so desperately needed—an active therapy for cancer.

There is a significant need in the art for a satisfactory treatment of cancer, and specifically lung, ovarian, breast, brain, colon and prostate cancers, which incorporates the benefits of TKI therapy, while obviating the resistance developed in response thereto by many patients, and overcoming the non-responsiveness exhibited by still other patients. Such a treatment could have a dramatic impact on the health of individuals, and especially older individuals, among whom cancer is especially common.

SUMMARY OF THE INVENTION

Embodiments of the present invention provide a therapy for the treatment of disease conditions, such as cancer, and, in particular, for the treatment of cancer in individuals who have developed a resistance to conventional TKI therapy or who are not responsive thereto ab initio. Described herein is a method that is surprisingly effective in treating cancer, and especially prostate, breast, lung, ovarian, brain and colon cancers, after such a resistance manifests or in patients who are not responsive to conventional TKI therapy; dramatically hindering or even reversing the progression of this disease. The method includes administering to patients a resistance-surmounting quantity of a TKI, which may be administered with less frequency than conventional TKI treatments. While not wishing to be bound by any theory, it is believed that this variant treatment regimen effectively blocks different members of the HER-kinase family. Standard dosing of a TKI is effective at blocking activation of EGFR, but intermittent, increased dosages of a TKI may block HER-2, as well as EGFR; thereby effecting a clinical benefit (i.e., tumor responses) in patients that do not respond to standard daily dosing of a TKI.

Further embodiments of the present invention describe diagnostic methods by which one can assess an individual's sensitivity to TKI therapy by analyzing that individual's expression level of one of the genes believed to be responsible for the resistance. The inventor has identified epithelial membrane protein-1 (EMP-1) as such a gene. Thus, if the individual expresses EMP-1 to a degree sufficient for resistance, then there may be an increased likelihood that the individual will not respond to therapy. However, an absence or relatively lower expression level of EMP-1 (i.e., a level of expression lower than the degree indicative of resistance) may infer a greater potential sensitivity to the treatment.

BRIEF DESCRIPTION OF THE DRAWINGS

FIG. 6C illustrates the direct effect of IRESSA on P-EGFR in accordance with an embodiment of the present invention.

DETAILED DESCRIPTION OF THE INVENTION

Figure 1:
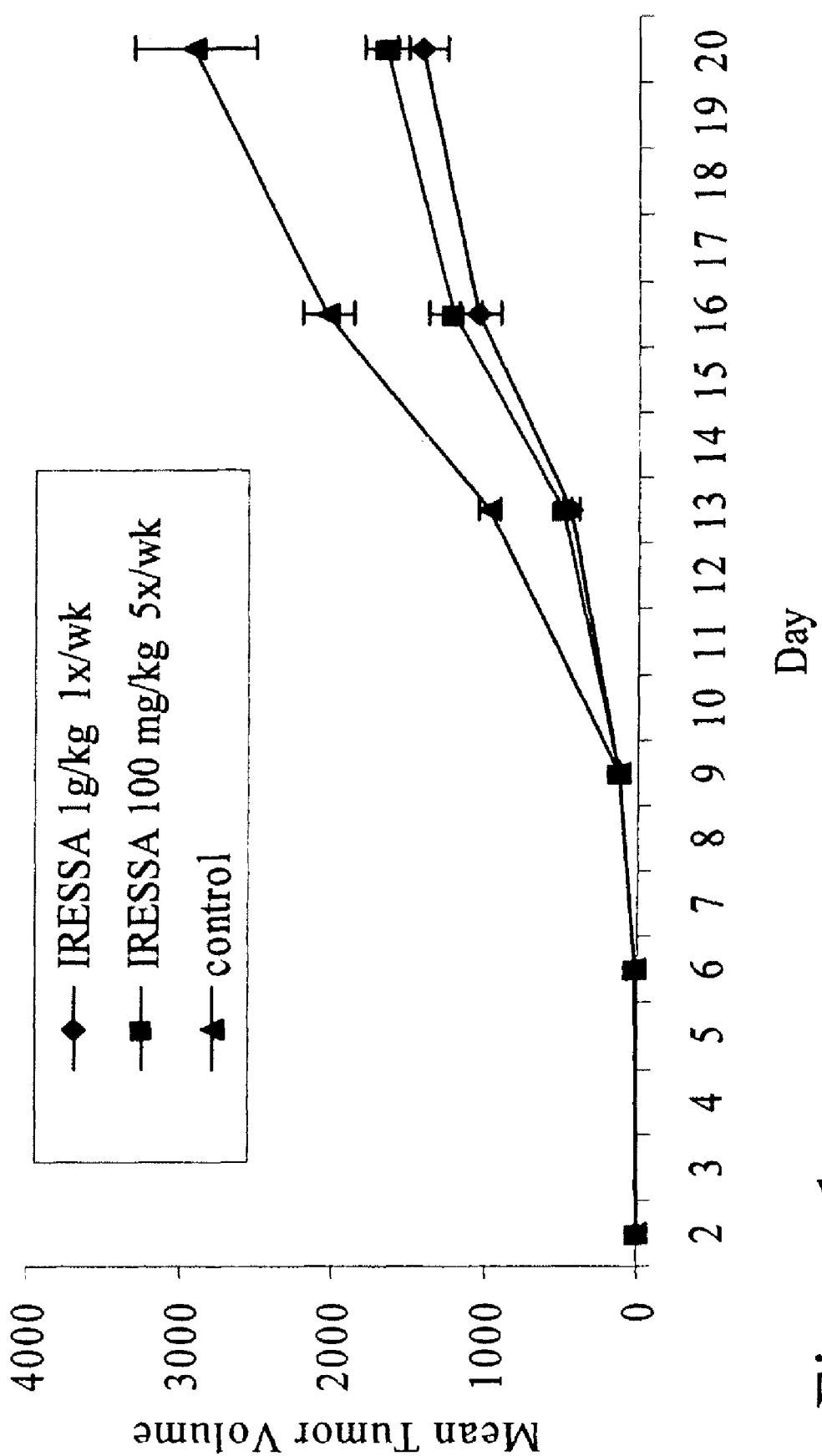
FIG. 1 depicts a graphical comparison (including mathematical standard error) of bolus dosing (1 g/kg) of a TKI (IRESSA) once per week compared with dosing of the same TKI five times per week in a conventional dosing regimen in accordance with an embodiment of the present invention. A control (i.e., no TKI administered) is graphically depicted as well. This experiment was performed in an androgen-independent prostate xenograft model. Equivalent growth inhibition was seen with daily or bolus dosing. The daily dosing was at the maximally tolerated dosage in the mice.

Conventional TKI therapies, such as IRESSA and TARCEVA, as discussed above, are indicated for administration to patients in a daily regimen for the treatment of cancer at dosages intended to block activation of EGFR. However, also as discussed above, patients frequently develop a resistance to this treatment. The present invention is based on the inventor's surprising discovery that a variant dosing regimen of a TKI may be administered to resistant patients to overcome their resistance, or to patients who are not responsive to TKI therapy ab initio to overcome their non-responsiveness (both indications are hereinafter included in the term "resistant" when used to describe individuals with cancer). This dosing schedule is surprisingly well-tolerated; increased dosages of daily TKI are generally not well-tolerated. Further embodiments of the present invention are based on the inventor's identification of EMP-1 as a gene responsible for this resistance or non-responsiveness.

Notably, the methods of the present invention are not limited to the treatment of cancer. Instead, it will be readily understood that the biomolecular pathways addressed and the TKI resistance obviated by the methods of the present invention may find application in the treatment of other disease conditions; any disease condition in which treatment with a TKI would result in a beneficial result for a patient under treatment. "Beneficial results" may include, but are in no way limited to, lessening the severity of the disease condition, preventing the disease condition from worsening, curing the disease condition and prolonging a patient's life or life expectancy. These disease conditions may relate to or be modulated by EGFR, HER-2 kinase or any other kinase that may be clinically affected with the methods of the present invention.

More specifically, the inventor's experimental studies have demonstrated clinical activity of TKIs at the daily dosing regimens in his xenograft models, and molecular studies on these tumors demonstrated effective inhibition of the EGFR signaling cascade. This confirmed that the xenograft models properly reflected the behavior of these TKIs as observed in other model systems. The inventor also surprisingly demonstrated that weekly IRESSA dosages at an amount significantly greater than the recommended daily dosing was well tolerated and can inhibit tumor growth effectively in the xenograft models—even in tumors that demonstrated a resistance to conventional TKI therapy. While not wishing to be bound by any theory, it is believed that these higher weekly doses inhibit both HER-2 kinase as well as EGFR, or HER-1 kinase; whereas conventional dosing only inhibits HER-1 kinase. Since it is further believed that the co-stimulatory effect (i.e., heterodimerization) of the HER-2 kinase with another member of the kinase family (e.g., HER-1, HER-3 or HER-4) is required for stimulation of the cell signaling pathways responsible for cell proliferation, it is also believed that the additional inhibition of the HER-2 kinase by the variant dosing regimen of the present invention is effective in inhibiting or downregulating this cell signaling. Moreover, even those patients who are resistant to conventional TKI therapy (which only affects HER-1) may obtain a beneficial, anti-tumor effect by the variant dosing regimen of the present invention, because the HER-2 kinase is inhibited as well. The increased dosages of the present invention may be associated with a lack of inhibitory specificity, resulting in a hindrance of the disease condition where conventional TKI therapies failed. The methods of the present invention, therefore, can overcome resistance or non-responsiveness to TKI therapy by operating differently than conventional methods at the cellular and molecular level.

In particular embodiments, a once- or twice-weekly increased dosage of a TKI may be effective in treating cancer, and especially lung, breast and prostate cancer, in an individual who is resistant to conventional TKI therapy. Other forms of cancer that may be treated with the methods of the present invention include, but are in no way limited to gastric, colorectal, and ovarian cancer, as well as glioblastoma tumors. Each of these forms of cancer demonstrates significant EGFR expression, making them suitable targets for treatment in accordance with the methods of the present invention.

TKIs suitable for use in accordance with the methods of the present invention may include, but are in no way limited to, TKIs that are generally known for use in the treatment of cancer, and, specifically, breast, lung and prostate cancer. By way of example, such TKIs may include IRESSA and TARCEVA, as described above, but may further include CI1033 (available from Pfizer Inc.), PKI166 (available from Novartis AG), GW2016 (available from GlaxoSmithKline), EKB569 (available from Wyeth), IMC-C225 (available from ImClone Systems Inc. and Bristol-Myers Squibb Co.), and pharmaceutically acceptable salts or equivalents of the same; each of the latter group currently at the Phase I or Phase II clinical trial stage, all of which are included within the term "kinase inhibitors" or "TKIs." In particular, any TKI that blocks EGFRs (e.g., HER-1) or any other HER family receptor (e.g., HER-2, HER-3, HERA) may be utilized, since it is believed that the blocking of these EGFRs and other receptors is the biomolecular means by which TKIs function to hinder or prevent the growth of lung, breast and prostate tumors as well as tumors associated with other types of cancer.

In an embodiment of the present invention, a TKI may be administered to a patient with cancer who is resistant to conventional TKI therapy in a "resistance-surmounting quantity," which, for purposes of the present invention, is defined as an amount of from about 500 mg to about 3,000 mg, administered as a bolus once or twice per week. The appropriate specific dosage of the TKIs of various embodiments of the present invention depends on the age and weight of the individual to be treated, whether the compound is being used as single agent or adjuvant therapy, the type of cancer (e.g., whether it is an adenocarcinoma, sarcoma, squamous cell carcinoma, ductal transitional carcinoma, or other prostate cancer), the progression of the cancer (e.g., whether it has metastasized or is localized), the nature of the tumor(s) to be treated (e.g., size, location, etc.) and other factors well known to those skilled in the art of oncology. In general, intermittent (i.e., weekly or semi-weekly) doses of between about 500 mg and 3,000 mg may be used (depending on the particular TKI); doses of between about 1,500 mg and 3,000 mg are preferred for most cases; doses of about 2,000 mg are further preferred. The administration of either IRESSA or TARCEVA at a single dose of about 2,000 mg per week may be especially effective. The selection of an appropriate pharmaceutical TKI and an appropriate dosage can be readily performed by one of skill in the art.

Functionally, the particular dosage may be selected to effect at least one of several internal biological conditions. First, the dosage may be selected to block the HER-2 kinase, either in addition to or in lieu of blocking the HER-1, or EGFR, kinase. Second, the dosage may be selected to yield a serum concentration of greater than about 800 $\mu$M of the TKI. Third, the dosage may be selected to block a kinase receptor other than EGFR or HER-2 to produce an anti-cancer treatment modality. A dosage within the above-described range may effect at least one of these biological conditions; however, it will be readily understood by one of skill in the art that not all of these conditions must be satisfied for the methods of the present invention to be effective in the treatment of cancer. Moreover, a dosage outside the above-identified range that effects these biological conditions is considered to be within the scope of the present invention. For instance, a particular route of pharmaceutical administration may necessitate the use of a dosage substantially outside the above-described range, yet if such a dosage effects the biological conditions described herein, it is considered to be within the scope of the present invention.

One may administer TKI compounds of the present invention orally, although one can also administer them by intravenous and intramuscular injection. In one embodiment, IRESSA or TARCEVA is administered orally in a bolus of about 2,000 mg once per week.

Figure 8:
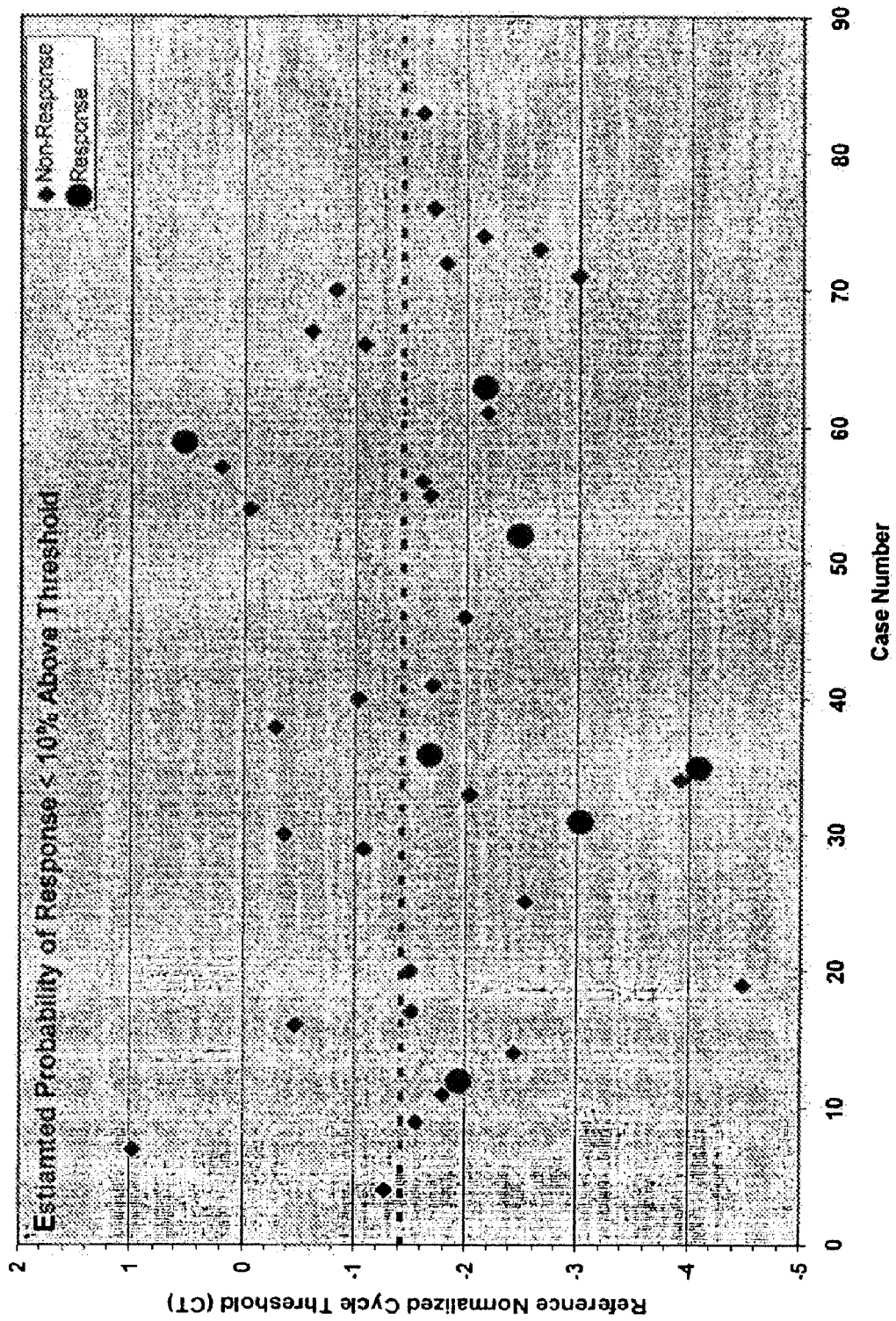
FIG. 8 depicts a case-by-case clinical response to TKI (IRESSA) therapy compared with patient EMP-1 expression level in accordance with an embodiment of the present invention. This data is from patients with non-small cell lung cancer treated with IRESSA; their clinical response was correlated with EMP-1 expression level. The probability of response to TKI (IRESSA) therapy was less than 10% in individuals whose EMP-1 expression level was above the threshold (i.e., dotted line) indicated (i.e., gene was "detectable" at the mRNA or protein levels, as assessed by TAQ-MAN technology).

Again, while not wishing to be bound by any theory, it is further believed that the mechanism responsible for resistance may be the expression or over-expression of EMP-1; this gene was found to be more strongly expressed in animals resistant to conventional TKI therapy, as discussed in greater detail in the Examples section below. Therefore, another embodiment of the present invention includes a diagnostic method for determining an individual's sensitivity to TKI therapy by screening their expression level of EMP-1. An individual with a relatively higher expression level of EMP-1 is likely to be resistant or non-responsive or to develop a resistance or non-responsiveness to TKI therapy. Conversely, an individual with a relatively lower expression level of EMP-1 is less likely to be resistant or non-responsive or to develop a resistance or non-responsiveness to TKI therapy. This is graphically illustrated in FIG. 9; although the data presented therein refer to RNA expression in tumors of patients with lung cancer who were administered IRESSA and whose response was correlated with EMP-1 expression level. Individuals that are likely to be resistant or non-responsive to TKI therapy may be particularly good candidates for administration of the resistance-surmounting quantity of TKI therapy once or twice a week, as described above. In particular, individuals who have a quantifiable expression level of EMP-1 (i.e., the gene is "detectable" or "turned on") have less than a 10% probability of responding to TKI therapy (FIG. 8).

To assess an individual's expression level of EMP-1, any conventional method known to those of skill in the art may be utilized. By way of example, one may use TAQMAN quantitative PCR of frozen tissue to look for RNA expression or TAQMAN quantitative PCR of RNA extracted from paraffin blocks to look for RNA expression (TAQMAN is available from Applied Biosystems; Foster City, Calif.). EMP-1 mRNA is illustrated herein as SEQ ID NO:1. Alternatively, one may use immunohistochemistry of paraffin sections stained with labeled antibodies to EMP-1 to look for protein expression. The procedures for employing any of these illustrative methodologies, as well as other conventional methodologies not specifically enumerated herein, are both well known to those of skill in the art and may be readily implemented without undue experimentation.

EXAMPLES

Figure 2:
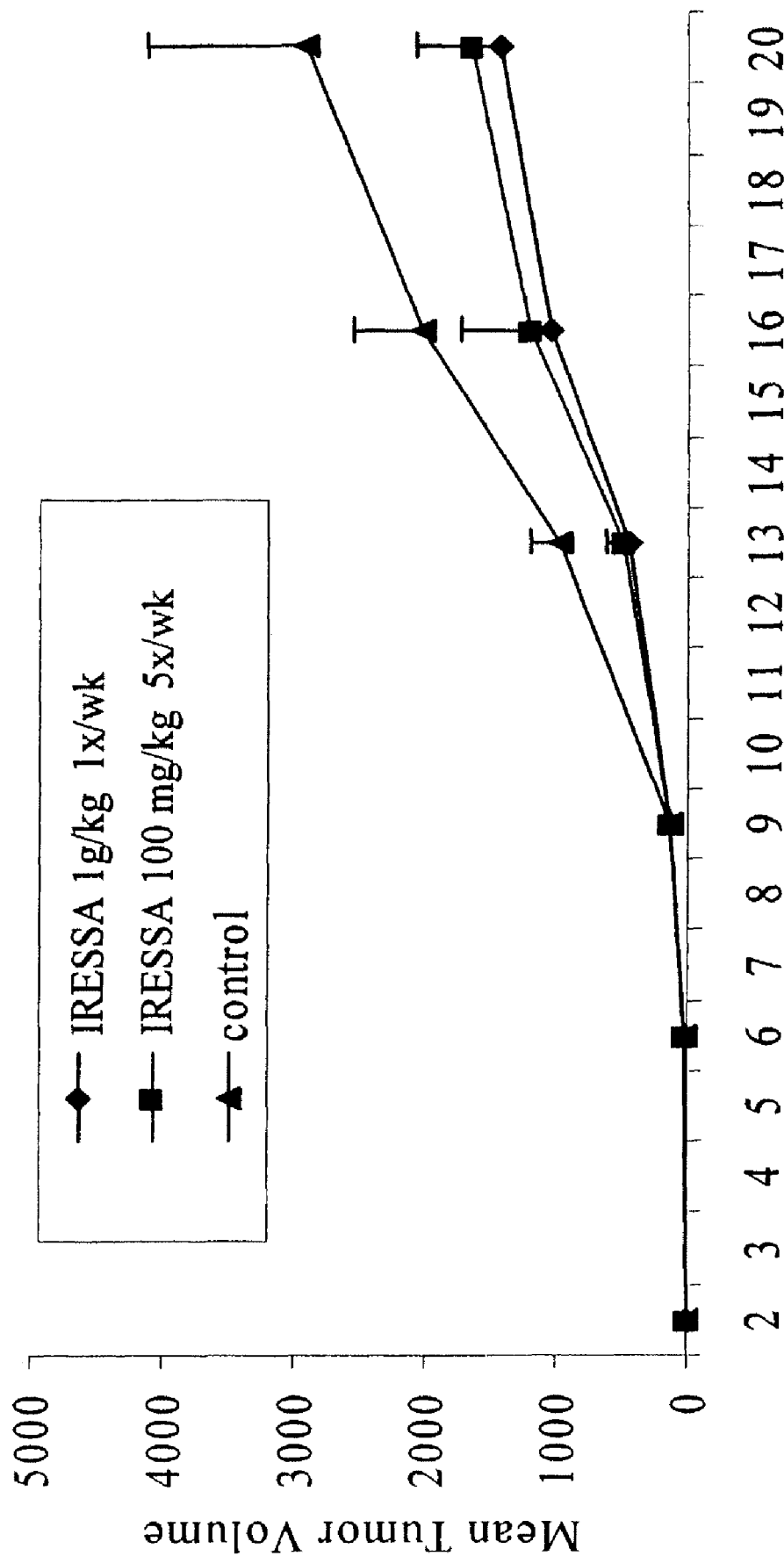
FIG. 2 depicts a graphical comparison (including mathematical standard deviation) of bolus dosing (1 g/kg) of a TKI (IRESSA) once per week compared with dosing of the same TKI five times per week in a conventional dosing regimen in accordance with an embodiment of the present invention. A control (i.e., no TKI administered) is graphically depicted as well. This experiment was performed in an androgen-independent prostate xenograft model. Equivalent growth inhibition was seen with daily or bolus dosing. The daily dosing was at the maximally tolerated dosage in the mice.
Figure 3A:
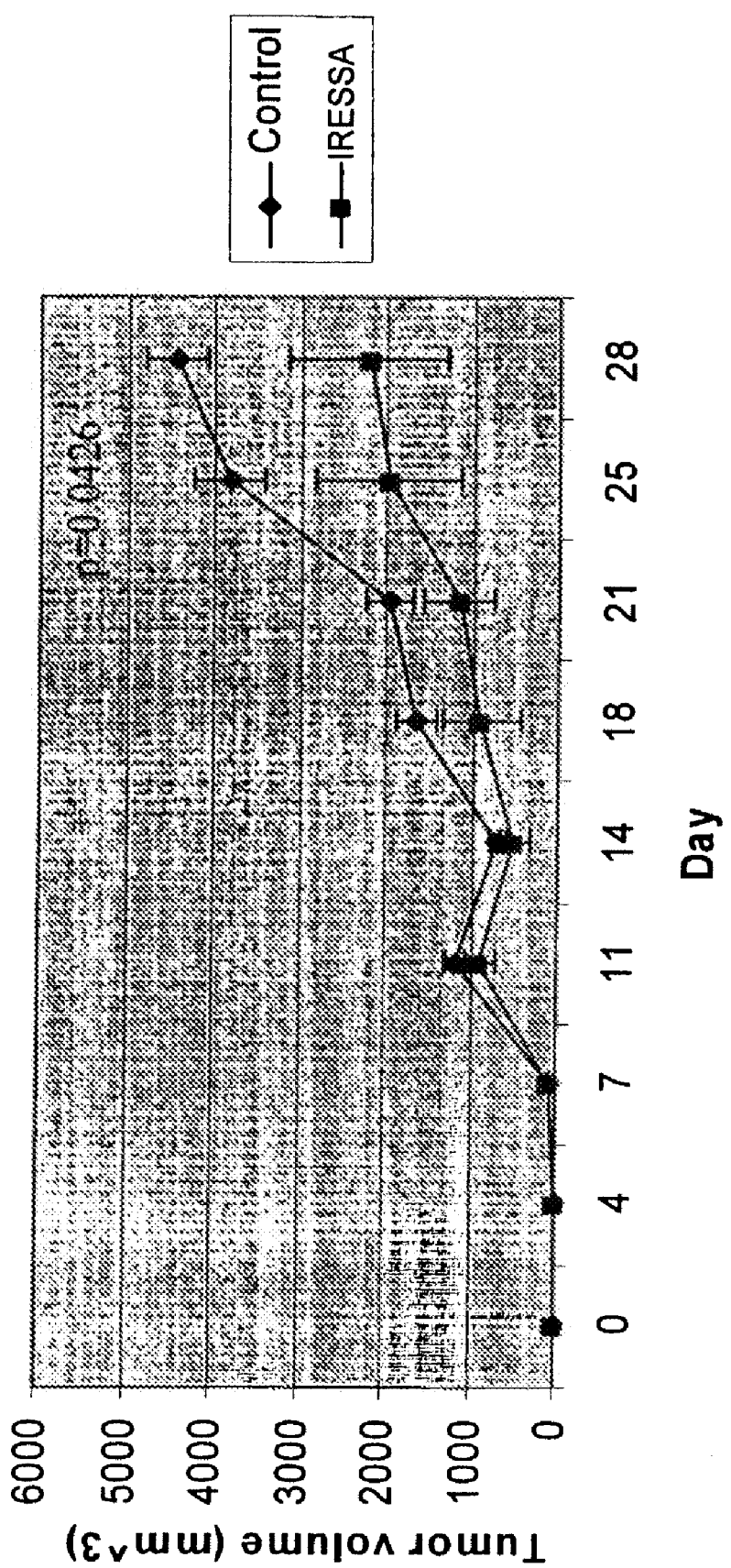
FIG. 3 depicts a graphical comparison of subcutaneous xenograft tumor volume in animals treated with a TKI (IRESSA) as opposed to control animals that received no TKI therapy in accordance with an embodiment of the present invention. Reduction of approximately 51% in androgen-dependent (CWR22) tumor volume (FIG. 3A) and approximately 66.4% in androgen-independent (CWR22R) tumor volume (FIG. 3B) was indicated for animals that received TKI therapy.
Figure 3B:
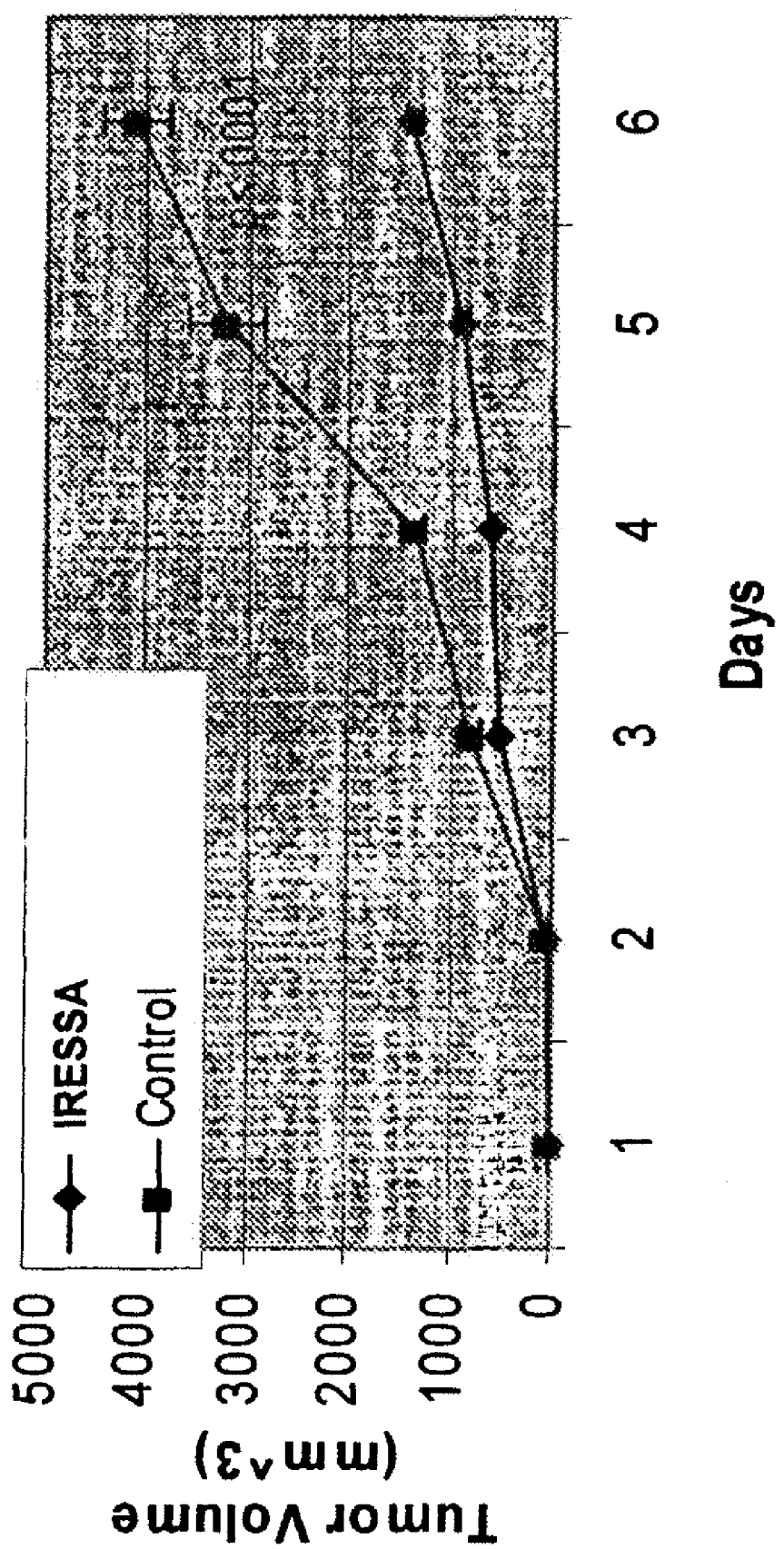

The following Examples show that animals can develop a resistance to conventional TKI therapy, but that a variant dosage of a TKI may overcome this resistance. In particular, a resistance-surmounting quantity of the TKI administered either once or twice per week may be effective to both overcome the resistance and to treat the underlying disease condition. This is graphically depicted in FIGS. 1 and 2, each of which illustrate a comparison of dosing with 100 mg/kg IRESSA five times per week as compared with weekly bolus dosing with 1 g/kg IRESSA once per week (FIG. 1 includes standard error and FIG. 2 includes standard deviation information).

The Examples further describe a diagnostic method whereby an individual's expression level of EMP-1 is used to screen the individual's resistance to TKI therapy. The Examples demonstrate the efficacy of the methods of the present invention with respect to androgen-independent prostate cancer xenografts, although similar experiments have been performed with respect to breast cancer, ovarian cancer and lung cancer xenograft models.

Example 1

Preparation of Prostate Cancer Xenograft

IRESSA targets the HER-kinase axis by competing for the ATP binding site on the EGFR molecule, as described above. It has previously been demonstrated to inhibit growth of epithelial cancer xenograft, including prostate tumors. To validate those observations and to also confirm a working model of IRESSA treatment, 8-10 week old athymic nude mice bearing subcutaneous androgen-dependent (CWR22) or androgen-independent (CWR22R) xenograft tumors were administered a daily oral treatment of IRESSA at a dose of 100 mg/kg for three weeks. A significant reduction in tumor volumes was observed (FIGS. 1 and 2) for both the CWR22 (about 50%) and CWR22R (about 66.4%) models; thereby validating the efficacy of IRESSA in androgen-independent prostate cancer.

Paraffin-embedded sections of the IRESSA-treated tumors were assessed for a decrease in cell proliferation and/or increase in cell apoptosis (data not shown), as these have been previously reported as possible outcomes of IRESSA treatment. No dramatic differences between treated and untreated controls were observed in either of the two assays, even though there was a statistically significant decrease in tumor volume following IRESSA treatment. This may have been due to the fact that the 50-70% decrease in tumor volume in this tumor model is the net result of both cell proliferation rate and apoptosis occurring simultaneously. However, at the molecular level, IRESSA did cause a marked inhibition of EGFR phosphorylation and subsequent ERK-1/2 phosphorylation, as expected.

Example 2

Development of an In Vivo IRESSA-Resistant Model

Figure 4A:
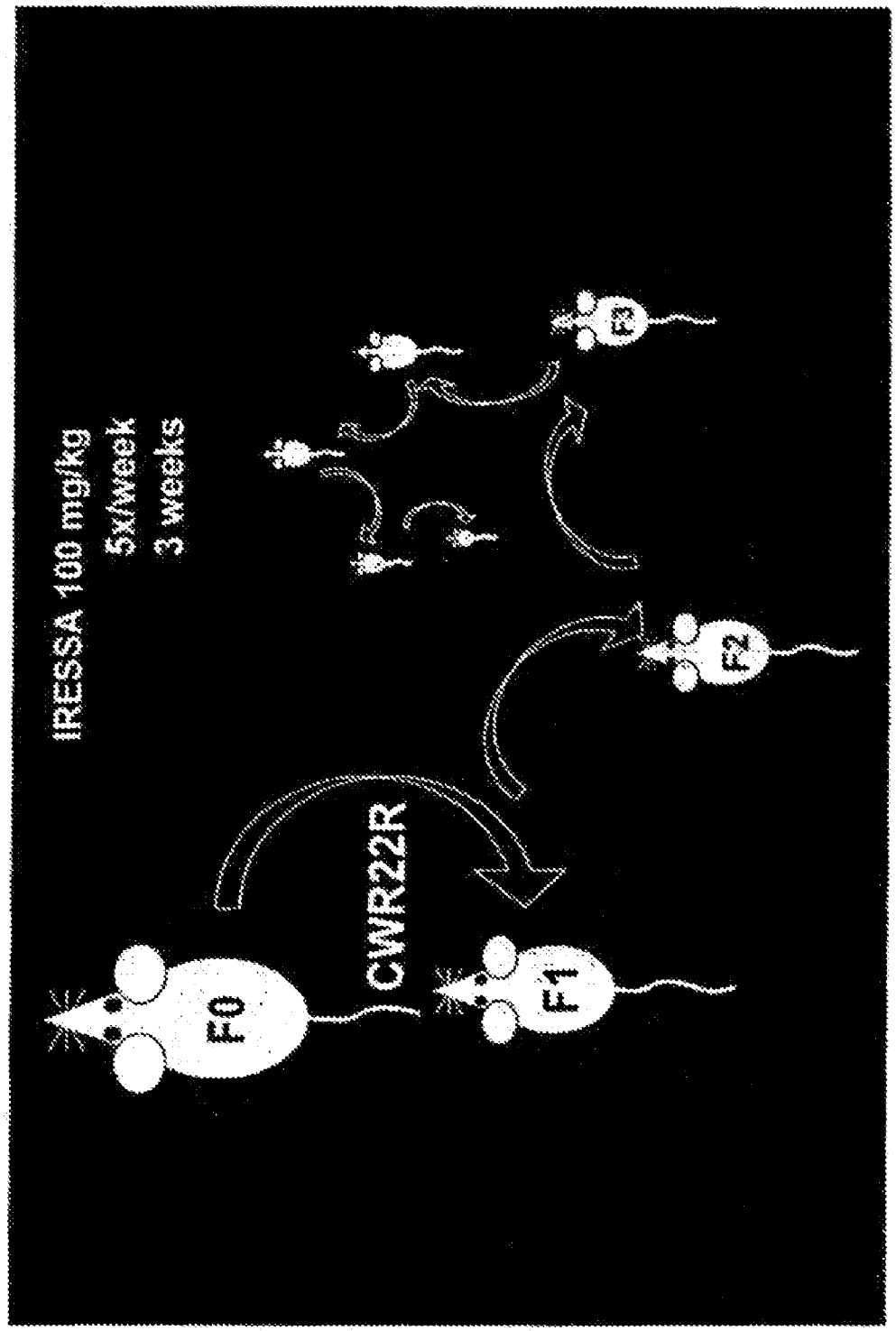
FIG. 4A depicts a scheme to develop two separate IRESSA-resistant (IR) tumor lines (CWR22R, CWRSA6) by serially passaging tumors in accordance with an embodiment of the present invention.

Having identified an androgen-independent prostate cancer model that is sensitive to IRESSA treatment, a corresponding IRESSA-resistant (IR) model was developed to evaluate the mechanisms of resistance with this drug. This was done by serially passaging IRESSA-treated CWR22R tumors in female athymic nude mice for twelve generations (FIG. 4A).

Figure 4B:
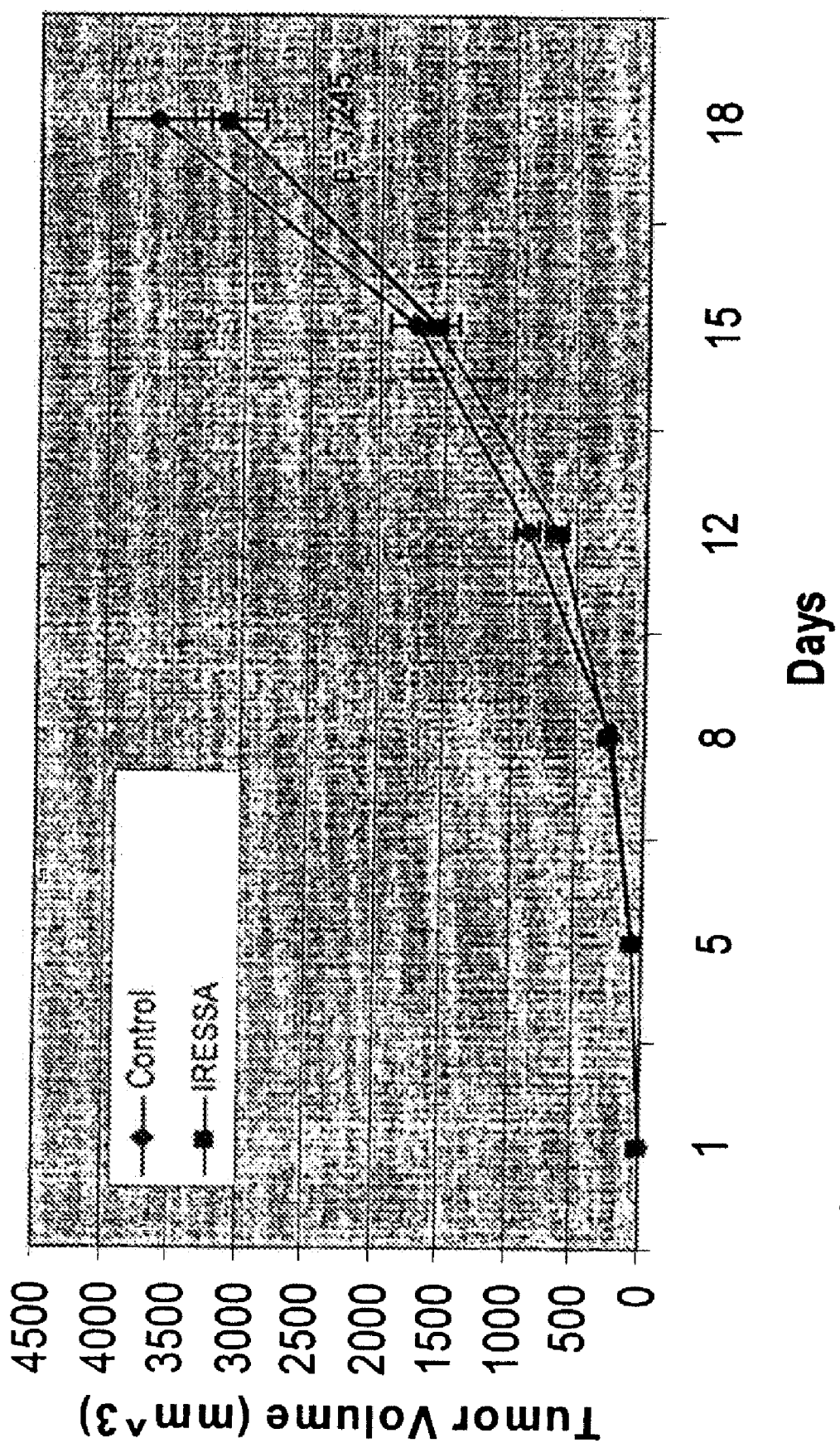
FIG. 4B depicts a graphical representation of an IRESSA resistance challenge in accordance with an embodiment of the present invention. IR tumors treated with IRESSA exhibited growth similar to untreated parental tumors.

CWR22R tumors, which first received IRESSA treatment at the initiation of the series, were termed "generation F0." Generation F0-F3 demonstrated sensitivity to IRESSA after three weeks of treatment (as evaluated by tumor growth curves); similar to that of the native CWR22R tumors. However, by generation F4, tumors demonstrated growth despite the presence of IRESSA. At generation F8, the tumors were characterized as "resistant" after a challenge experiment showed IRESSA to be ineffective in inhibiting tumor growth on two independently derived IR lines as compared to the F0 parental tumors (FIG. 4B). Two separately derived, IR lines were developed.

Example 3

IR Tumors CWR22R Tumors are Sensitive to 2C4

Figure 5:
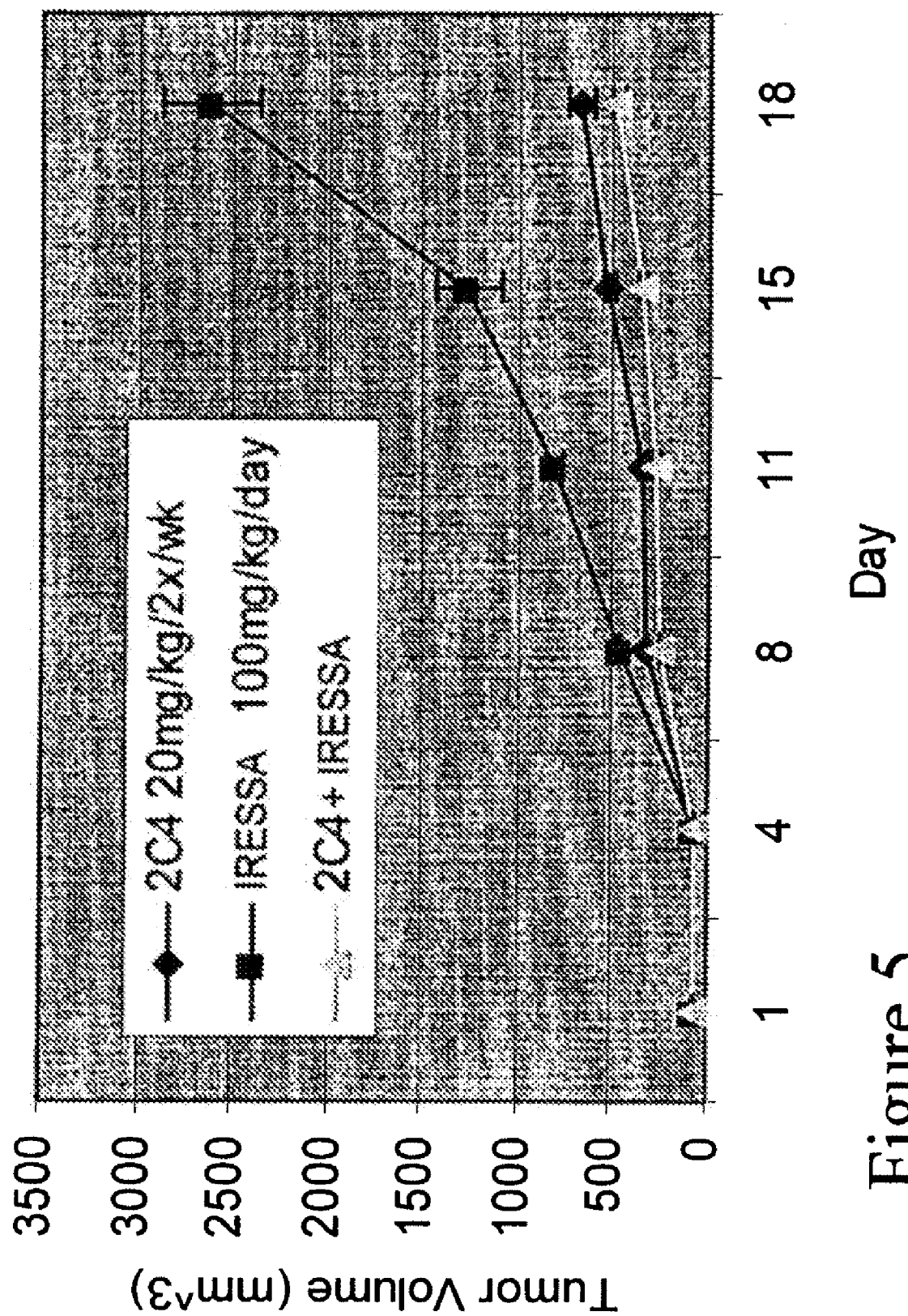
FIG. 5 depicts a graphical representation of IR tumors treated with the monoclonal antibody 2C4 (available from Genentech, Inc.; hereinafter "2C4"), and showing an 81% growth inhibition as compared to IR tumors receiving IRESSA therapy in accordance with an embodiment of the present invention. Additionally, tumors treated with a combination of IRESSA and 2C4 resulted in a similar tumor growth curve as 2C4 alone (statistically insignificant difference).

There was a possibility that the serial passaging of tumors coupled with the continuous presence of IRESSA had caused irreversible "damage" to the HER-kinase axis (i.e., a non-functional EGFR pathway, and thus, the observed resistance). To rule out this possibility as a reason for resistance in this model, the IR tumor at generation F12 was treated with either IRESSA (100 mg/kg/day) or 2C4 (20 mg/kg/2×/wk). 2C4 is a monoclonal antibody against HER-2 that prevents its heterodimerization with HER-1, HER-3 or HERA, and, consequently, inhibits tumor growth by ablating ligand-mediated signaling. Remarkably, after a two-week treatment period, the IR tumors receiving 2C4 showed an 81% growth inhibition as compared to those receiving IRESSA (FIG. 5).

A combination of 2C4 and IRESSA resulted in a similar growth curve as 2C4 alone, suggesting that IRESSA was unable to potentiate the 2C4 effect. These results conclusively prove that the HER-kinase axis was still functional in this IR model, and that the acquired IRESSA resistance was not due to the lack of signaling via this pathway. It also strengthens the paradigm that IRESSA and 2C4 target distinct molecules in the EGFR pathway.

Example 4

IR CWR22R Tumor has Functional EGFR

Figure 6A:
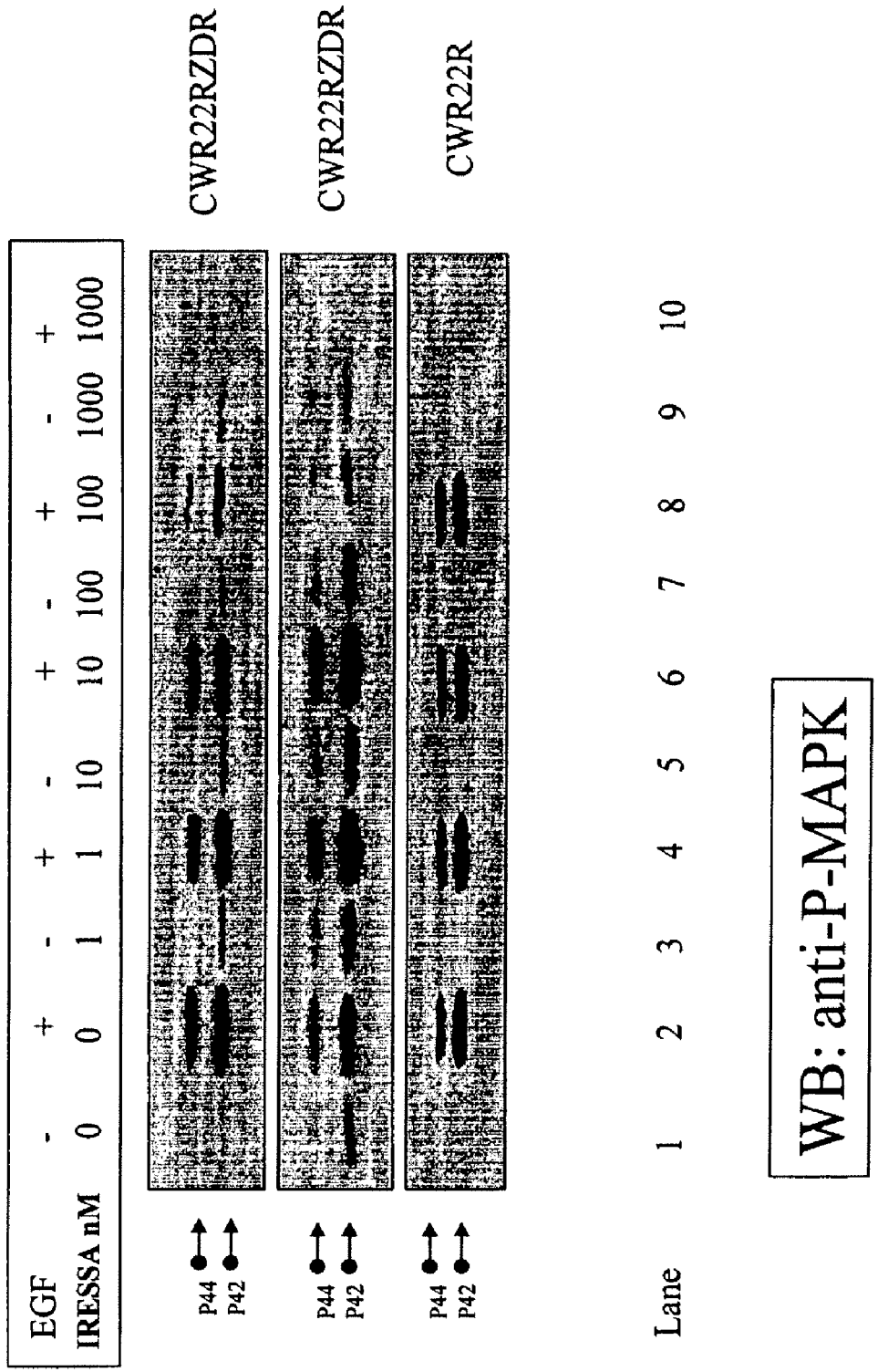
FIG. 6A illustrates the ability of EGF to activate MAPK to equivalent levels in both IRESSA-sensitive and IR tumors in accordance with an embodiment of the present invention.
Figure 6B:
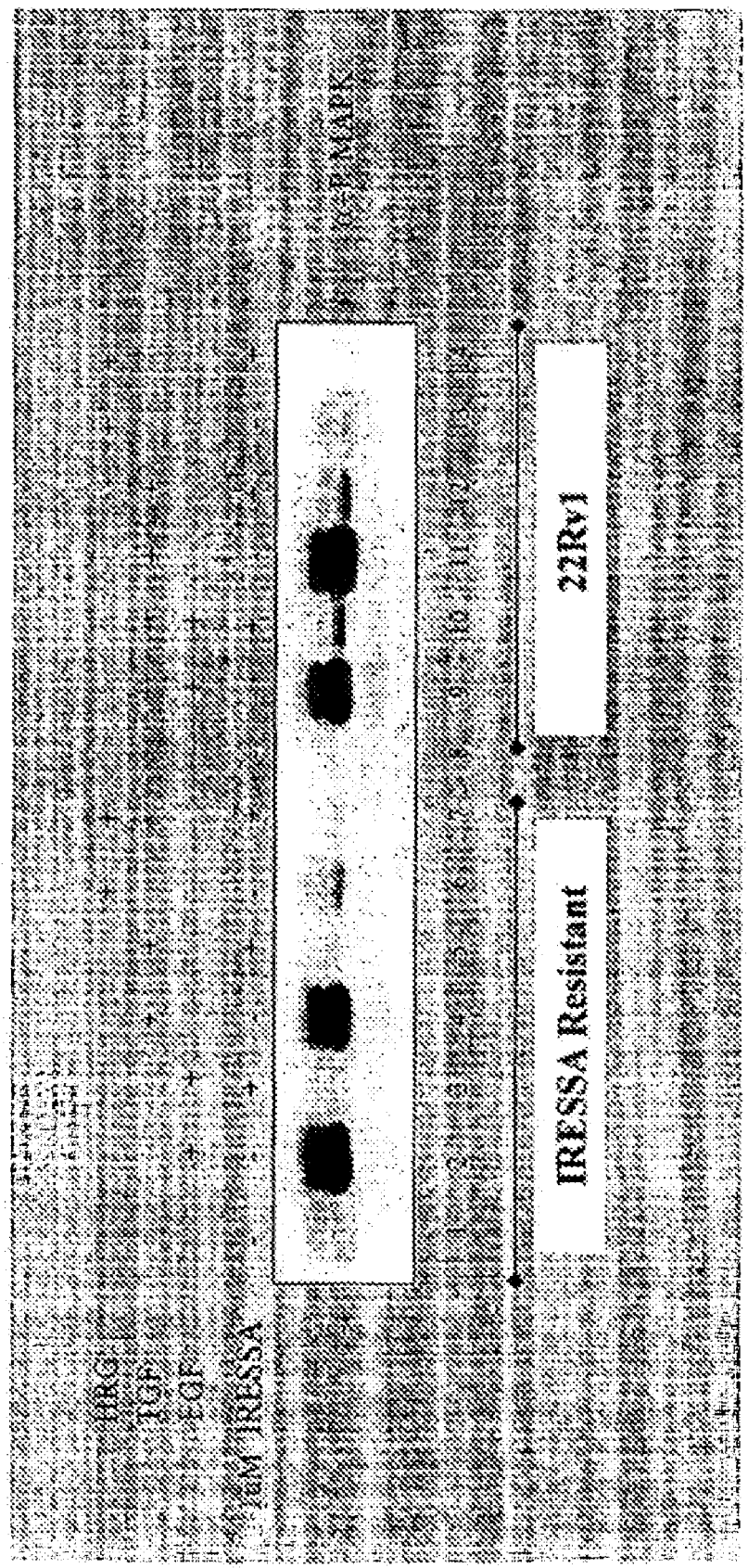
FIG. 6B illustrates IRESSA inhibition of p-MAPK on IR cells stimulated with TGF-$\alpha$ in accordance with an embodiment of the present invention.

To ascertain whether the IR xenografts had a functional EGFR (i.e., whether the surrogate marker, phosphorylated mitogen activated protein kinase (p-MAPK), could be stimulated with an appropriate ligand), tumor cells (from both IRESSA-sensitive and IR tumors) were cultured ex vivo and starved of growth factors for 18-24 hours. They were then treated with a dose curve of either IRESSA or the vehicle, and stimulated with epidermal growth factor (EGF). As shown in FIG. 6A, EGF was able to activate MAPK to equivalent levels in both tumor types, suggesting that the EGFR molecule was functional. Increasing doses of IRESSA suppressed ligand-stimulated MAPK at 100-1000 nM in cells derived from the sensitive CWR22R model. Surprisingly, IR ex vivo cells followed the same pattern of MAPK inhibition as the sensitive cells; thus corroborating that the EGFR pathway was intact in the IR model; that the $IC_{50}$ for p-MAPK inhibition did not increase in the resistant line; and that the resistance did not lead to a constitutive activation of this signaling mechanism. IRESSA inhibition of p-MAPK on IR cells was also evident on transforming growth factor-α (TGF-α)-stimulated cells (FIG. 6B); another ligand for EGFR. A cell line derived from the CWR22R xenograft, 22Rv1, was used as a control.

The direct effect of IRESSA on phosphorylated-EGFR (p-EGFR) was also evaluated. This was first carried out on 22Rv1 cells (FIG. 6C). p-EGFR was clearly upregulated upon EGF stimulation, and this effect could be completely blocked with 10 nM IRESSA ($IC_{50}$ for EGFR is <0.015-0.05 μM).

Example 5

Iressa Resistance not a Result of Target Gene Amplification or Upregulation of Constitutively Active EGFRvIII Mutant Overexpression of EGFR in human malignancy has been the subject of extensive study, in which it has become increasingly apparent that amplification of EGFR may be important with respect to the oncogenic effects; such alterations have been demonstrated to correlate with a poor prognosis. Moreover, amplification of target genes is frequently used as a mechanism to generate drug resistance in neoplastic cells (Goker et al., *Blood*, vol. 86:677-684 (1995)). For example, BCR-ABL overexpression due to gene amplification has been suggested as one of the mechanisms for GLEEVEC resistance (Various Authors, *Science: Technical Comments*, vol. 293:2163a (2001)). These observations prompted the inventor to question whether. EGFR overexpression developed in the IR line.

Figure 7A:
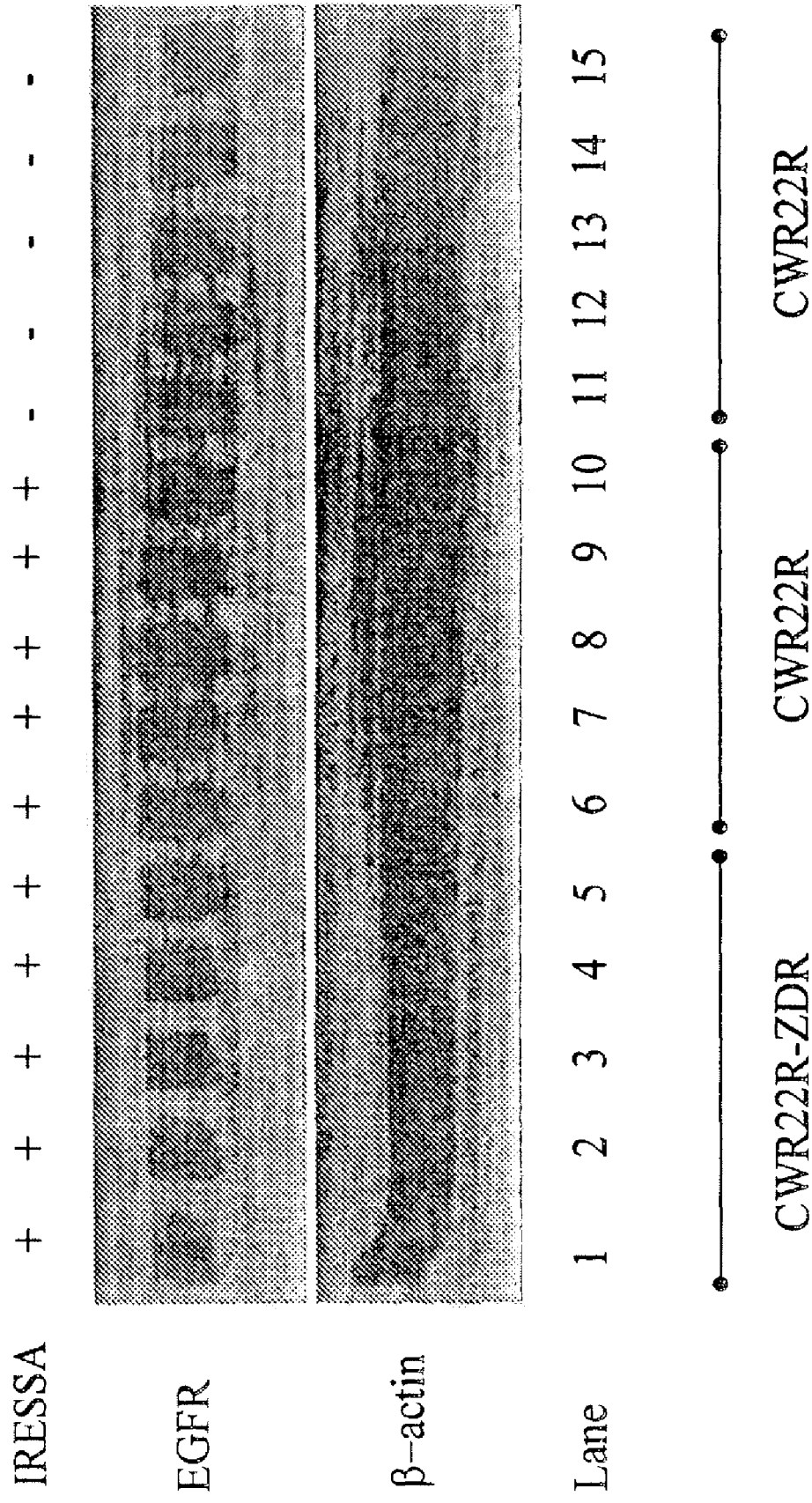
FIG. 7A illustrates that total EGFR protein remained unchanged in IR tumors in accordance with an embodiment of the present invention.
Figure 7B:
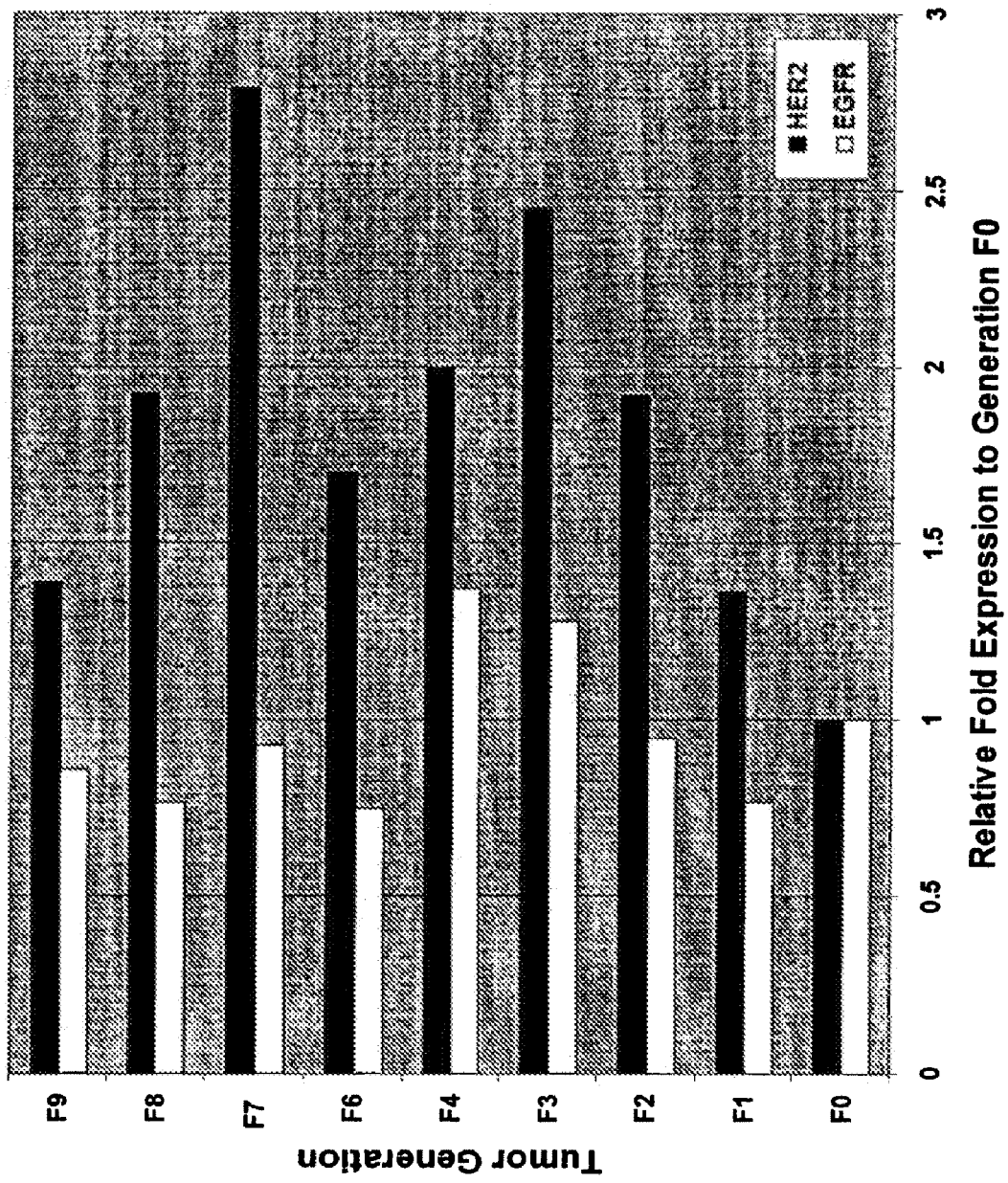
FIG. 7B illustrates that EGFR and HER-2 mRNA remained unchanged in IR tumors in accordance with an embodiment of the present invention.

Total EGFR protein remained unchanged in the IR tumors, as shown in FIG. 7A EGFR (HER-1) mRNA and HER-2 mRNA (the secondary target for IRESSA), also remained unchanged as determined by a real time quantitative reverse transcription polymerase chain reaction (RT-PCR) analysis (FIG. 7B).

Since there were similar levels of receptor mRNAs between the two lines, the possibility of EGFR (HER-1) or HER-2 gene amplification in the IR model was ruled out. The expression levels of other members of the HER-kinase axis, namely, HER-3, HER-4, EGF, TGF-α and heregulin (HRG) were also examined. They were equivalent between the sensitive and resistant lines (data not shown).

Another possibility for the resistance mechanism may have been the upregulation of the constitutively active EGFR class III variant, EGFRvIII. EGFRvIII lacks 267 amino acids from its extracellular domain and has been reported in glioblastoma multiforme, breast, ovarian, prostate and lung carcinomas. The likelihood of this molecule being upregulated in the IR model was small, because there is no evidence for regulation of EGFRvIII by EGF and TGF-α. However, the ex vivo cells derived from the IR line clearly demonstrated ligand stimulation at the molecular level (FIG. 6A). Nevertheless, no difference in EGFRvIII expression changes between the sensitive and IR tumors were found by TAQMAN PCR analysis (data not shown).

Example 6

Iressa Resistance and MDR1

The major multidrug transporters, MDR1 and MRP1, are involved in cancer drug resistance by extruding a large variety of hydrophobic compounds. Overexpression of MDR1 was evaluated in the IR line both at the mRNA as well as the protein level. The expression of MDR1 in the IR tumor was equivalent to that in the sensitive tumor. Similar results were obtained when MDR1 was analyzed in the ex vivo cells derived from the respective tumors. In the xenograft model, the IR cells were still able to respond to EGF, as determined by the stimulation of MAPK; further supporting the absence of MDR1 overexpression. That this effect can be suppressed by IRESSA at a concentration equivalent to that for the sensitive cells argues against the presence of a drug efflux pump in the resistant cells.

Example 7

Resistance not a Consequence of Mutations within ATP Binding Region of EGFR and HER-2 Tyrosine Kinase Domains The resistance mechanism of GLEEVEC has been a subject of intense study for the past few years. Although it is believed that the resistance mechanism may be multifactorial, one component of the resistance mechanism has been described as a point mutation (T315I) within the ATP-binding pocket of its target gene, BCR-ABL (Shah et al., *Cancer Cell*, vol. 2(2):117-25 (2002)). This mutation was initially described in CML patients who had GLEEVEC-refractory disease or who had a relapse during the treatment (Roumiantsev et al., *Proc. Natl. Acad. Sci. USA*, vol. 99(16):10700-05 (2002)).

Since IRESSA is also a competitive inhibitor of ATP binding sites within the tyrosine kinase domains of EGFR and HER-2 ($IC_{50}$ for EGFR is <0.015-0.05 μM and $IC_{50}$ for HER-2 is 1.2-3.7 μM), it was reasoned that resistance could be due to mutations within the kinase region of the target receptors required for IRESSA binding and, thus, inhibition. The tyrosine kinase domains of both HER-2 and EGFR were sequenced using sequencing primers SEQ ID NO:2 (HER-2 forward primer for 5' end of gene), SEQ ID NO:3 (HER-2 reverse primer for 5' end of gene), SEQ ID NO:4 (HER-2 forward primer for 3' end of gene), SEQ ID NO:5 (HER-2 reverse primer for 3' end of gene), SEQ ID NO:6 (EGFR forward primer for 5' end of gene), SEQ ID NO:7 (EGFR reverse primer for 5' end of gene), SEQ ID NO:8 (EGFR forward primer for 3' end of gene) and SEQ ID NO:9 (EGFR reverse primer for 3' end of gene).

These regions also include the ATP binding sites for the respective receptors. Analysis of the sequence data for tumors F0-F9 did not identify any consistent mutations within the resistant tumors; thus ruling out the possibility of any kinase region mutations contributing to the resistance mechanism. The catalytic tyrosine kinase domains from the resistant tumors were also subcloned into TOPO cloning vectors (available from Invitrogen Corporation; Carlsbad, Calif.) and resequenced to confirm the absence of mutations.

Example 8

Gene Expression Profiles of IR Tumors Reveals EMP-1

Figure 9:
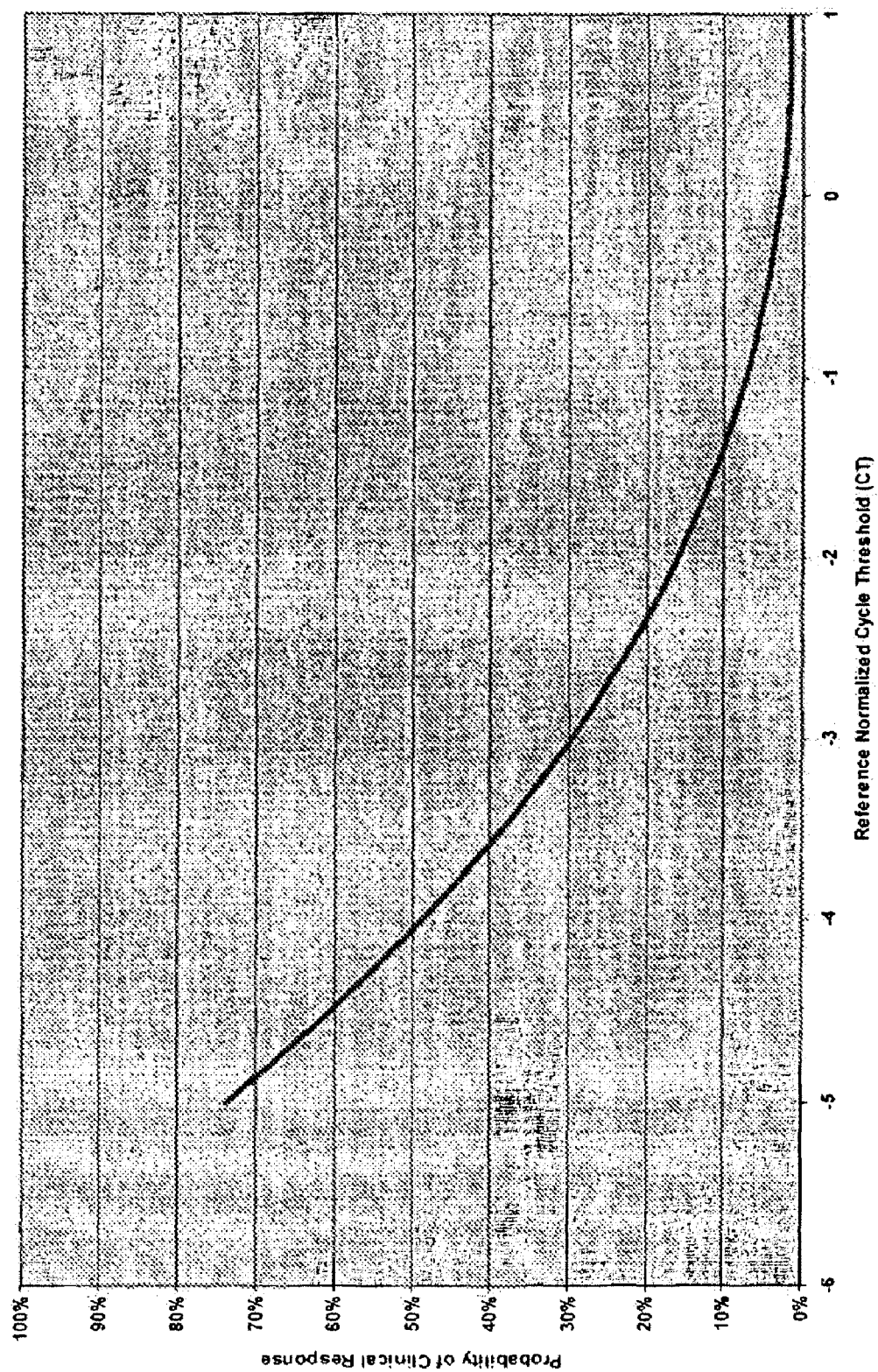
FIG. 9 depicts a graphical comparison of the probability of response to TKI (IRESSA) therapy against patient EMP-1 expression level in accordance with an embodiment of the present invention. This data is from patients with non-small cell lung cancer treated with IRESSA; their clinical response was correlated with EMP-1 expression level.

The gene expression profiles of IR tumors were analyzed by gene chip analysis, using the gene arrays described in Alon et al., *Proc. Natl. Acad. Sci. USA*, vol. 96(12):6745-50 (1999). Native tumors and tumors from generation F8 of both IR lines as well as native tumors treated with IRESSA for 12 hours were chipped. After statistical analysis, 96 genes were identified in the IR tumors as having changed more than 20-fold as compared to native tumors (data not shown). A strong correlation with lack of clinical response to IRESSA and presence of EMP-1 RNA was demonstrated (FIG. 8). Presence of EMP-1 RNA was assessed with TAQMAN from paraffin samples. Moreover, the probability of an individual responding to TKI therapy decreases as EMP-1 expression level increases (FIG. 9).

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of screening an individual with prostate or lung cancer for sensitivity to gefitinib therapy, comprising:
    obtaining a tumor sample from the individual with prostate or lung cancer;
    contacting the tumor sample with a nucleic acid probe for epithelial membrane protein 1 (EMP-1);
    examining an expression level of EMP-1 mRNA the tumor sample;
    caring the expression level of EMP-1 mRNA of the tumor sample to an expression level of EMP-1 mRNA of a gefitinib sensitive prostate or lung tumor; and
    determining the prostate or lung cancer is resistant or non-responsive to conventional gefitinib therapy when the expression level of EMP-1 mRNA of the tumor sample is 20-fold or higher than the expression level of EMP-1 mRNA of the gefitinib sensitive prostate or lung tumor.

2. The method of claim 1, wherein the individual has prostate cancer.

3. The method of claim 1, wherein the individual has lung cancer.

4. The method of claim 1, wherein the nucleic acid probe is on a gene chip.

* * * * *

SEQUENCE LISTING

<160> NUMBER OF SEQ ID NOS: 9

<210> SEQ ID NO 1
<211> LENGTH: 2786
<212> TYPE: DNA
<213> ORGANISM: Homo sapiens

<400> SEQUENCE: 1

```
agcactctcc agcctctcac cgcaaaatta cacacccag  tacaccagca gaggaaactt     60
ataacctcgg gaggcgggtc cttcccctca gtgcggtcac atacttccag aagagcggac    120
cagggctgct gccagcacct gccactcaga gcgcctctgt cgctgggacc cttcagaact    180
ctctttgctc acaagttacc aaaaaaaaaa gagccaacat gttggtattg ctggctggta    240
tctttgtggt ccacatcgct actgttatta tgctatttgt tagcaccatt gccaatgtct    300
ggttggtttc caatacggta gatgcatcag taggtctttg gaaaaactgt accaacatta    360
gctgcagtga cagcctgtca tatgccagtg aagatgccct caagacagtg caggccttca    420
tgattctctc tatcatcttc tgtgtcattg ccctcctggt cttcgtgttc cagctcttca    480
ccatggagaa gggaaaccgg ttcttcctct caggggccac cacactggtg tgctggctgt    540
gcattcttgt ggggtgtcc atctacacta gtcattatgc gaatcgtgat ggaacgcagt    600
atcaccacgg ctattcctac atcctgggct ggatctgctt ctgcttcagc ttcatcatcg    660
gcgttctcta tctggtcctg agaaagaaat aaggccggac gagttcatgg ggatctgggg    720
ggtggggagg aggaagccgt tgaatctggg agggaagtgg aggttgctgt acaggaaaaa    780
ccgagatagg ggaggggggga ggggaagca aaggggggag gtcaaatccc aaaccattac    840 tgagggatt ctctactgcc aagcccctgc cctggggaga aagtagttgg ctagtacttt    900
gatgctccct tgatggggtc cagagagcct ccctgcagcc accagacttg gcctccagct    960
gttcttagtg acacacactg tctggggccc catcagctgc cacaacacca gccccacttc   1020
tgggtcatgc actgaggtcc acagacctac tgcactgagt taaaatagcg gtacaagttc   1080
tggcaagagc agatactgtc tttgtgctga atacgctaag cctggaagcc atcctgccct   1140
tctgacccaa agcaaaacat cacattccag tctgaagtgc ctactggggg gctttggcct   1200
```

-continued

```
gtgagccatt gtccctcttt ggaacagata tttagctctg tggaattcag tgacaaaatg    1260
ggaggaggaa agagagtttg taaggtcatg ctggtgggtt agctaaacca agaaggagac    1320
cttttcacaa tggaaaacct gggggatggt cagagcccag tcgagacctc acacacggct    1380
gtccctcatg gagacctcat gccatggtct ttgctaggcc tcttgctgaa agccaaggca    1440
gctcttctgg agtttctcta aagtcactag tgaacaattc ggtggtaaaa gtaccacaca    1500
aactatggga tccaaggggc agtcttgcaa cagtgccatg ttagggttat gttttagga    1560 ttcccctcaa tgcagtcagt gtttcttta agtatacaac aggagagaga tggacatggc     1620
tcattgtagc acaatcctat tactcttcct ctaacatttt tgaggaagtt ttgtctaatt    1680
atcaatattg aggatcaggg ctcctaggct cagtggtagc tctggcttag acaccacctg    1740
gagtgatcac ctcttgggga ccctgcctat cccacttcac aggtgaggca tggcaattct    1800
ggaagctgat taaacacac ataaaccaaa accaaacaac aggcccttgg gtgaaaggtg      1860
ctatataatt gtgaagtatt aagcctaccg tatttcagcc atgataagaa cagagtgcct    1920
gcattcccag gaaaatacga aaatcccatg agataaataa aaatataggt gatgggcaga    1980
tcttttcttt aaaataaaaa agcaaaaact cttgtggtac ctagtcagat ggtagacgag    2040
ctgtctgctg ccgcaggagc acctctatac aggacttaga agtagtatgt tattcctggt    2100
taagcaggca ttgctttgcc ctggagcagc tattttaagc catctcagat tctgtctaaa    2160 ggggttttt gggaagacgt tttctttatc gccctgagaa gatctacccc agggagaatc     2220
tgagacatct tgcctacttt tctttattag cttttctcctc atccatttct tttataccctt   2280 tccttttttgg ggagttgtta tgccatgatt tttggtattt atgtaaaagg attattacta   2340
attctatttc tctatgttta ttctagttaa ggaaatgttg agggcaagcc accaaattac    2400
ctaggctgag gttagagaga ttggccagca aaaactgtgg gaagatgaac tttgtcatta    2460
tgatttcatt atcacatgat tatagaaggc tgtcttagtg caaaaaacat acttacatttt   2520 cagacatatc caagggaat actcacatttt tgttaagaag ttgaactatg actggagtaa   2580
accatgtatt cccttatctt ttactttttt tctgtgacat ttatgtctca tgtaatttgc    2640
attactctgg tggattgttc tagtactgta ttgggcttct tcgttaatag attatttcat    2700
atactataat tgtaaatatt ttgatacaaa tgtttataac tctagggata taaaaacaga    2760
ttctgattcc cttcaaaaaa aaaaaa                                        2786
```

```
<210> SEQ ID NO 2
<211> LENGTH: 18
<212> TYPE: DNA
<213> ORGANISM: Homo sapiens

<400> SEQUENCE: 2
cagcagaaga tccggaag                                                   18

<210> SEQ ID NO 3
<211> LENGTH: 19
<212> TYPE: DNA
<213> ORGANISM: Homo sapiens

<400> SEQUENCE: 3
agcccgaagt ctgtaattt                                                  19

<210> SEQ ID NO 4
<211> LENGTH: 18
<212> TYPE: DNA
```

-continued

```
<213> ORGANISM: Homo sapiens

<400> SEQUENCE: 4
ctgctgaact ggtgtatg                                                 18

<210> SEQ ID NO 5
<211> LENGTH: 18
<212> TYPE: DNA
<213> ORGANISM: Homo sapiens

<400> SEQUENCE: 5
tccagcagtg agcggtag                                                 18

<210> SEQ ID NO 6
<211> LENGTH: 19
<212> TYPE: DNA
<213> ORGANISM: Homo sapiens

<400> SEQUENCE: 6
ccaagctctc ttgaggatc                                                19

<210> SEQ ID NO 7
<211> LENGTH: 18
<212> TYPE: DNA
<213> ORGANISM: Homo sapiens

<400> SEQUENCE: 7
aagcgacggt cctccaag                                                 18

<210> SEQ ID NO 8
<211> LENGTH: 18
<212> TYPE: DNA
<213> ORGANISM: Homo sapiens

<400> SEQUENCE: 8
ctggactatg tccgggaa                                                 18

<210> SEQ ID NO 9
<211> LENGTH: 19
<212> TYPE: DNA
<213> ORGANISM: Homo sapiens

<400> SEQUENCE: 9
ggccattttg gagaattcg                                                19
```